United States Patent [19]

Rocktäschel et al.

[11] 3,947,436

[45] Mar. 30, 1976

[54] SULFUR CONTAINING ORGANO-ORGANOOXYSILANE

[75] Inventors: Gottfried Rocktäschel; Friedrich Thurn; Horst Fleischhauer, all of Grossauheim; Werner Schwarze, Frankfurt am Main; Hermann Westlinning, Kleinostheim, all of Germany

[73] Assignee: Deutsche Gold- und Silber-Scheideanstalt vormals Roessler, Germany

[22] Filed: Mar. 14, 1974

[21] Appl. No.: 451,290

Related U.S. Application Data

[63] Continuation-in-part of Ser. No. 163,467, July 16, 1971, Pat. No. 3,798,196.

[30] Foreign Application Priority Data

July 18, 1970 Germany............................ 2035778

[52] U.S. Cl... 260/249.5; 260/248 CS; 260/302 SD; 260/42.15
[51] Int. Cl.²................ C07D 251/46; C07D 251/38
[58] Field of Search.................. 260/248 CS, 249.5

[56] References Cited
UNITED STATES PATENTS

| | | |
|---|---|---|
| 3,328,451 | 6/1967 | Bulbenko........................ 260/448.8 |
| 3,388,144 | 6/1968 | Musolf............................. 260/448.8 |
| 3,445,496 | 5/1969 | Ryan................................ 260/448.8 |
| 3,781,291 | 12/1973 | Sulzbach et al................ 260/248 X |

FOREIGN PATENTS OR APPLICATIONS

| | | |
|---|---|---|
| 684,993 | 12/1952 | United Kingdom |
| 778,272 | 7/1957 | United Kingdom |
| 869,844 | 6/1961 | United Kingdom |
| 970,598 | 9/1964 | United Kingdom |
| 1,018,311 | 1/1966 | United Kingdom |
| 1,113,228 | 5/1968 | United Kingdom |
| 1,549,723 | 11/1968 | France |
| 1,173,898 | 7/1964 | Germany |
| 2,031,473 | 1/1971 | Germany |
| 357,972 | 7/1973 | Sweden |

*Primary Examiner*—John M. Ford
*Attorney, Agent, or Firm*—Cushman, Darby & Cushman

[57] ABSTRACT

There are prepared sulfur containing organoorganooxysilanes of the formula A-X-Z where A is R-S—, where R is a triazine or thiodiazole residue, X is a divalent organic residue, Z is -SiR'' (OR')$_2$; -Si(OR')$_3$; -Si(OR')$_2$-O-Si(OR')$_3$; -Si(OR')$_2$-O-Si(OR')$_2$-X-A; where R' and R'' are alkyl groups of 1 to 12 carbon atoms. The compounds are useful as additives to cross-linkable mixtures containing organic polymers.

14 Claims, No Drawings

SULFUR CONTAINING ORGANO-ORGANOOXYSILANE

This application is a continuation-in-part of application Ser. No. 163,467, filed July 16, 1971 now U.S. Pat. No. 3,798,196, the entire disclosure of which is hereby incorporated by reference.

The invention relates to useful sulfur containing organo-organooxysilanes exerting two important functions and their use in rubber mixtures.

The addition reaction of silicon compounds containing at least one hydrogen atom bound to silicon to nonaromatic carbon to carbon double and triple bonds is known in the literature. This addition reaction proceeds, for example, from trichlorosilane and a double bond containing substance according to the following formula:

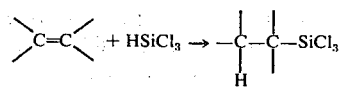

As catalysts for this reaction platinum compounds have many advantages, for example there can be used dichloroplatinum (IV) acetyl acetonate (see German Auslegeschrift 1,271,712 and corresponding Knorre et al U.S. Pat. 3,470,225 the entire disclosures of which are hereby incorporated by reference).

If there are used for example as the unsaturated organic starting compounds the industrially easily available allyl halides the addition of trichlorosilane using the above named special platinum containing catalysts proceeds according to the following equation to form 3-halogenpropyl trichlorosilanes $$\text{Hal-CH}_2\text{-CH=CH}_2 + \text{HSiCl}_3 \rightarrow \text{Hal-CH}_2\text{-CH}_2\text{-CH}_2\text{-SiCl}_3$$

where Hal is Cl, Br, I.

The halogenorgano halosilanes formed can be reacted with various alcohols. There are formed halogenorgano organooxysilanes, for example using the above mentioned 3-halogenpropyltrichlorosilanes a reaction occurs according to the following equation $$\text{Hal-(CH}_2)_3\text{-SiCl}_3 + 3 \text{ R}^i\text{OH} \rightarrow \text{Hal-(CH}_2)_3\text{-Si(OR}^i)_3 + 3 \text{ H-Hal}$$

where $R^i$ is an organic group attached to the alcoholic hydroxyl group. There are formed accordingly 3-halogenpropyltrialkoxysilanes. The alkoxysilanes are also designated as oxysilanes (see Ullmanns Enzyklopadie der Technischen Chemie, Vol. 15 (1964) page 762).

The halogenorgano-organooxysilanes can also be formed from the reaction product of silicochloroform and a preferably lower monovalent alcohol which can be added to unsaturated halohydrocarbons according to the equation $$\text{Hal-CH}_2\text{-CH=CH}_2 + \text{HSi(OR}^i)_3 \rightarrow \text{Hal-(CH}_2)_3\text{-Si(OR}^i)_3$$

In this reaction also platinum compounds are required as catalysts.

The sulfur containing organo-organooxysilanes of the invention are prepared by reaction of halogenorgano-organooxysilanes with organic sulfur compounds, preferably with metal or ammonium salts. The reaction proceeds according to the general equation $$\text{A-Me} + \text{Hal-X-Z} \rightarrow \text{A-X-Z} + \text{Me-Hal} \quad (I)$$

Reaction I is preferably carried out in solution, e.g. in an inert organic solvent. The solvent is preferably chosen so that the salt A-Me is soluble therein while on the contrary the salt Me-Hal formed in the reaction is slightly soluble or insoluble therein. The precipitated salt Me-Hal is filtered off and the sulfur containing organo-organooxysilane remains behind after removal of the solvent or it is recovered in pure form by vacuum distillation if it is not decomposed.

If the metal or ammonium salts of the starting compounds in special cases are not available the transformation can be carried out in the presence of hydrogen halide acceptors according to the following general equation $$\text{A-H} + \text{Hal-X-Z} + \text{Acceptor} \rightarrow \text{A-X-Z} + \text{H-Hal.Acceptor} \quad (II)$$

(Examples of acceptors are tertiary amines such as triethylamine, tripropylamine, etc.)

In the general equations (I) and (II) the terms have the following significance.

Me: ammonium, hydrocarbon substituted ammonium, e.g. tetramethyl ammonium, triethyl ammonium, diethyl ammonium, a metal of the alkali or alkaline earth metal group, e.g. sodium, potassium, rubidium, cesium, barium, calcium, strontium or magnesium, as well as manganese, iron, cobalt, nickel, zinc, cadmium or copper in equivalence to A, e.g. NaA or Ca($A_2$). Preferably Me signifies ammonium, sodium or potassium.

Hal: a halogen of the group of Cl, Br and I (i.e. halogen of atomic weight 35, 80 resp. 127); preferably chlorine or bromine (halogen of atomic weight 35 resp. 80).

X is a divalent hydrocarbon group, saturated or unsaturated, branched or straight chain, however, having at least 3 carbon atoms in the main chain, acyclic, cyclic with 3 to 18 carbon atoms whose hydrogen atoms in a given case can be substituted by fluorine, pseudohalogen (see Rompps Chemisches Worterbuch (1969) page 707, e.g. thiocyanate), phenyl, halophenyl (e.g. chlorophenyl or bromophenyl), alkyl or dialkylphenyl (in which the alkyl contains 1 to 3 carbon atoms), and in which the organic residue X can be interrupted by one or up to four heteroatoms (oxygen, nitrogen, sulfur and/or phosphorus) or can form a heterocyclic group with these hetero atoms; preferably X is -$CH_2$-($CH_2)_n$-$CH_2$- (n is 1 to 15, preferably 1 to 3).

A is a. N≡C-S-
b. R-S-
c. RO-CS-S-
d. RS-CS-S-
e. $R_1$-CS-S-

In the formulae (b) to (d) R indicates a univalent hydrocarbon group, saturated or unsaturated, branched or straight chain, acyclic or cyclic; a heterocyclic or heteroaromatic group; all these respectively with 1 to 15 carbon atoms and 1 to 5 heteroatoms from the group of nitrogen, oxygen and sulfur. In the formula (e) furthermore $R_1$ means

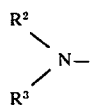

wherein R² and R³ (the same or different) are hydrogen, alkyl of 1 to 5 carbon atoms, benzyl, cycloalkyl with 5 to 7 carbon atoms or both together with the nitrogen atom form a ring having 5 to 8 atoms with up to one further nitrogen or oxygen or sulfur atom. Preferably R means hydrocarbon groups, saturated or unsaturated, e.g. ethylenically unsaturated, branched or straight chain with 1 to 8 carbon atoms or heterocyclic groups with up to 3 nitrogen atoms and in a given case having a side chain thereon a sulfur atom as well as in a given case a mercapto and/or amino group, which in the latter case can be substituted with lower alkyl groups, i.e. alkyl of 1 to 8 carbon atoms.

Z:

—SiR''(OR')₂; —Si(OR')₃;
—Si(OR')₂-O—Si(OR')₃;   —Si(OR')₂—N-H—Si(OR')₃;
—Si(OR')₂—O—Si(OR')₂—X—A;
—Si(OR')₂—NH—Si(OR')₂—X—A.

wherein R' and R'' are the same or different and have the following significance:

alkyl of 1 to 12 carbon atoms, preferably Z is
—Si(OCH₃)₃, —Si(OCH₂CH₃)₃, —Si(OCH₂CH₂CH₃)₃,

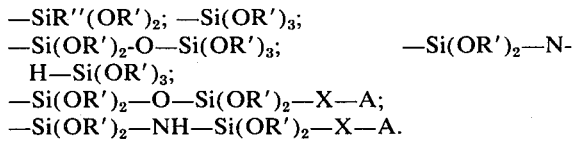

Preferably in the A portion of the molecule A-X-Z the group R signifies —CH₃; —CH₂CH₃; —CH₂CH₂CH₃; —CH(CH₃)₂; —CH₂CH₂CH₂CH₃; —CH₂—CH=CH₂;

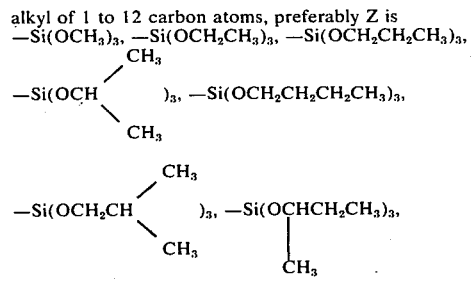

where R₄ and R₅ are hydrogen or lower alkyl, e.g. alkyl of 1 to 8 carbon atoms or phenyl.

For the group R₁ there are named H₂C=CH—CH₂—NH—; (H₂C=CH—CH₂)₂N-;

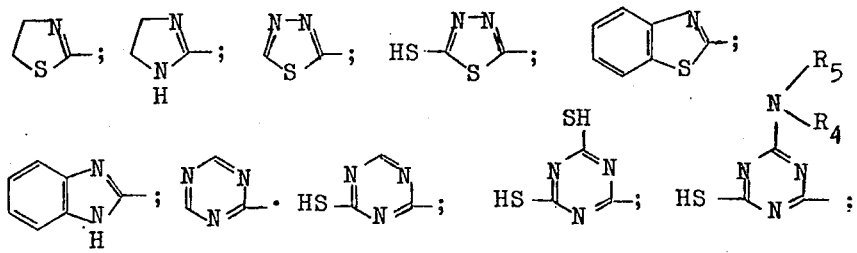

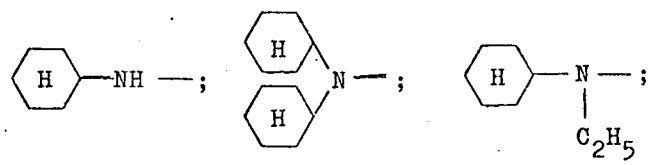

The first two named groups for R₁ are particularly advantageous.

The various sulfur containing organo-organooxysilane compounds of the invention in general can be obtained according to equations (I) and (II) by variation of the compound A-Me or the compound A-H without requiring a special synthesis for each new compound. The sulfur containing organo-organooxysilanes can be made industrially in a very favorable manner from inexpensive starting materials. The industrial applications of these compounds are therefore in a wide extent and in manyfold ways possible.

The sulfur containing organo-organooxysilanes are used advantageously as vulcanizing agents in the cross-linking of elastomers and as binding agents between inorganic fillers and organic polymers. Examples of elastomers include polyisoprene such as natural rubber, polyisoprene, polybutadiene, butadiene-styrene copolymer, butadiene-acrylonitrile copolymer, terpolymers such as polymers of ethylene-propylene-cyclooctadiene, ethylene-propylene-norbornadiene, ethylene-propylene-dicyclopentadiene, ethylene-propylene-cyclododecatriene, furthermore butyl rubber etc.

Examples of compounds within the present invention include 3-thiocyanatopropyl triethoxy silane, 3-thiocyanatopropyl trimethoxy silane, 3-thiocyanatopropyl tripropoxy silane, 3-thiocyanatopropyl diethoxy methyl silane, 3-thiocyanatopropyl tributoxy silane, 4-thiocyanatobutyl triethoxy silane, 6-thiocyanatohexyl triisopropoxy silane, 18-thiocyanatooctadecyl trimethoxy silane, 1,3-(3-thiocyanatopropyl)-1,1,3,3-tetramethoxy disiloxane, 1,3-(3-thiocyanatopropyl)-1,1,3,3-tetraethoxy disiloxane, 2-diethylamino-4-mercapto-6-(3-triethoxysilyl propyl)-thiotriazine, 2-dimethylamino-4-mercapto-6-(4-triisopropoxysilyl butyl)-thiotriazine, 2-amino-4-mercapto-6-(3-trimethoxysilyl propyl)-thiotriazine, 2-diphenylamino-4-mercapto-6-(5-tributoxysilyl amyl)-thiotriazine, 2-phenylamino-4-mercapto-6-(3-triethoxysilyl propyl)-thiotriazine, 2-butylamino-4-mercapto-6-(18-triethoxysilyl octadecyl)-thiotriazine, allylthiopropyl trimethoxy silane, pentadecenylthiopropyl trimethoxy silane, 2,4-dimercapto-6-(3-triethoxysilylpropyl)-thiotriazine, 2-mercapto-4-(3-triethoxysilyl propyl)-thiotriazine, 2-mercapto-4-(3-tripropoxysilyl propyl)-thiotriazine, 2-methyl-4-mercapto-6-(3-tributoxysilyl propyl)-thiotriazine, 2-mercapto-5-(3-triethoxysilyl propyl)-thio-1,3,4-thiadiazole, 3-triethoxysilylpropyl-ethyl-xanthogenate, 3-trimethoxysilylpropyl-ethyl-xanthogenate, 3-tripropoxysilylpropyl-ethyl-xanthogenate, 3-triisopropoxysilylpropyl-ethyl-xanthogenate, 3-tributoxysilylpropyl-ethyl-xanthogenate, 3-triethoxysilylpropyl-methyl-xanthogenate, 3-trimethoxysilylpropyl-propyl-xanthogenate, 3-trimethoxysilylpropyl-isodecyl-xanthogenate, 3-triethoxysilylpropyl-2'-ethyl hexyl-xanthogenate, 3-triethoxysilylpropyl-pentadecyl-xanthogenate, 3-triethoxysilylpropyl-allyl-xanthogenate, 4-tributoxysilylbutyl-ethyl-xanthogenate, 18-triethoxysilyloctadecyl-methyl-xanthogenate, 1,3-(3-S-thiocarbomethoxypropyl)-9-1,1,3,3-tetramethoxy disiloxane, 1,3-(3-S-thiocarboethoxypropyl)-1,1,3,3-tetraethoxy disiloxane, 3-triethoxysilylpropyl-ethyl-thioxanthogenate, 3-tripropoxysilylpropyl-methyl-thioxanthogenate, 3-triethoxysilylpropyl-isobutyl-thioxanthogenate, 3-triethoxysilylpropyl-allyl-thioxanthogenate, 1,3-(3-S-thiocarbomethylmercapto propyl)-1,1,3,3-tetramethoxy disiloxane, 3-triethoxysilyl-propyl-N-methyl-dithiocarbaminate, 3-trimethoxysilyl-propyl-N-ethyl-dithiocarbaminate, 3-tributoxysilyl-propyl-N-hexyl-dithiocarbaminate, 4-triisopropoxysilyl-butyl-N-octyl-dithiocarbaminate, 3-triethoxysilyl-propyl-N-allyl-dithiocarbaminate, 3-dipropoxymethylsilyl-propyl-N-allyl-dithiocarbaminate, 3-trimethoxysilyl-propyl-N-allyl-dithiocarbaminate, 3-triethoxysilyl-propyl-N,N-diallyl-dithiocarbaminate, 4-trimethoxysilyl-butyl-N,N-diallyl-dithiocarbaminate, 3-triethoxysilyl-propyl-N-cyclohexyl-dithiocarbaminate, 4-tripropoxysilyl-butyl-N,N-dicyclohexyl-dithiocarbaminate, 3-trimethoxysilyl-propyl-piperidino-dithiocarbaminate, 3-triethoxysilyl-propyl-morpholino-dithiocarbaminate, 3-triethoxysilyl-propyl-N,N-dibenzyl-dithiocarbaminate, 3-triethoxysilyl-propyl-N-cyclohexyl-N-ethyl-dithiocarbaminate, 1,3-(3-N,N-diallyl dithiocarbaminato propyl)-1,1,3,3-tetraisopropoxy disiloxane.

The new sulfur containing organo-organooxysilanes can be prepared in the manner disclosed below.

Unless otherwise indicated all parts and percentages are by weight.

EXAMPLE 1

3-thiocyanatopropyl triethoxy silane 272 grams of water free potassium thiocyanate were dissolved in 1500 ml. of dimethylformamide and heated to boiling. Then in th course of about 2 hours there were added dropwise 674 grams of 3-chloropropyl triethoxy silane. After a further 30 minutes heating the reaction according to the equation NCS—K + Cl—(CH$_2$)$_3$—Si(OC$_2$H$_5$)$_3$
→ NCS—(CH$_2$)$_3$—Si(OC$_2$H$_5$)$_3$ + KCl was ended. After cooling the separated potassium chloride was filtered off over a Seitz filter and after removing the solvent the 3-thiocyanatopropyl triethoxy silane was finally recovered by vacuum distillation. B.P.$_{0.12}$ 97°–98° C., yield about 85% based on the weight of the 3-chloropropyl triethoxy silane. The yield can be further increased by optimizing reaction conditions.

| Analysis | C | H | Si | N | S |
|---|---|---|---|---|---|
| Calculated (%) | 44.70 | 7.98 | 10.68 | 5.31 | 12.18 |
| Found (%) | 44.80 | 7.93 | 10.30 | 5.35 | 12.20 |

The 3-thiocyanatopropyl triethoxy silane was further defined by its IR-spectra characteristics.

EXAMPLE 2

3-triethoxysilylpropyl-ethyl-xanthogenate 80 grams of potassium ethyl xanthogenate were dissolved in 500 ml. of acetone and 120 grams of 3-chloropropyl triethoxy silane were added dropwise to this solution. The mixture was stirred for 5 days at room temperature. After this time the reaction according to the equation H$_5$C$_2$O—CS—SK + Cl—(CH$_2$)$_3$—Si(OC$_2$H$_5$)$_3$
→ H$_5$C$_2$O—CS—S—(CH$_2$)$_3$—Si(OC$_2$H$_5$)$_3$ + KCl was practically completed. The potassium chloride which precipitated was filtered off and the solvent removed by distillation. The yellow liquid remaining behind could not be distilled in vacuum without decomposition. Yield 82% based on the weight of the 3-chloropropyl triethoxy silane.

| Analysis | C | H | Si | Cl | S |
|---|---|---|---|---|---|
| Calculated (%) | 44.12 | 8.03 | 8.60 | — | 19.64 |
| Found (%) | 43.85 | 8.23 | 8.40 | 0.6 | 18.65 |

The reaction can also be carried out in ethanol as the reaction medium. In this case the sodium ethyl xanthogenate is advantageously produced in situ:

In 400 ml. of ethanol there were dissolved 23 grams of sodium metal, subsequently at 50° C. there were added 76 grams of carbon disulfide. After a short post reaction time there were added dropwise 241 grams of 3-chloropropyl triethoxy silane. After the end of the reaction the precipitated sodium chloride was filtered off and the mixture worked up as described above.

EXAMPLE 3

3-thiocyanatopropyl tri-n-butoxy silane

NCS—K + Cl(CH$_2$)$_3$—Si(OC$_4$H$_9$)$_3$
→ NCS—(CH$_2$)$_3$—Si(OC$_4$H$_9$)$_3$ + KCl 24.3 grams of potassium thiocyanate were dissolved in 900 ml. of n-butanol and the solution heated to boiling. Then there were added dropwise in about 30 minutes 81.3 grams of 3-chloropropyl tri-n-butoxy silane. After a further 20 hours of boiling at reflux temperature the precipitated potassium chloride was separated off with a Seitz filter. The solvent was distilled off from the filtrate and the 3-thiocyanatopropyl tri-n-butoxy silane distilled in vacuo. B.P.$_{0.1}$ 128°–129° C., yield 85% based on the weight of the 3-chloropropyl tri-n-butoxy silane.

| Analysis | C | H | Si | N | S |
|---|---|---|---|---|---|
| Calculated (%) | 55.50 | 9.49 | 8.20 | 4.01 | 9.20 |
| Found (%) | 54.61 | 9.26 | 7.90 | 3.90 | 9.00 |

EXAMPLE 4

2-diethylamino-4-mercapto-6-(3-triethoxysilylpropyl)-thiotriazine 27.1 grams of 2-diethylamino-4,6-dimercapto triazine were dissolved in 350 ml. of acetone and 15 grams of triethylamin were added as an HCl acceptor. Then the mixture was heated to boiling and in the course of 20 minutes there were added dropwise 30.1 grams of 3-chloropropyl triethoxy silane. After a further 20 hours the precipitated triethylammonium chloride was filtered off over a Seitz filter. The solvent was separated by distillation with the help of a vacuum. The reaction product is a crystalline mass which cannot be distilled even in high vacuum. Yield 94% based on the weight of the 3-chloropropyl triethoxy silane. The reaction product is apparantly a mixture of several triazine compounds with 0, 1 and 2 mercapto groups.

| Analysis | C | H | Si | N | S |
|---|---|---|---|---|---|
| Calculated (%) | 44.15 | 7.84 | 6.88 | 13.74 | 15.71 |
| Found (%) | 45.18 | 8.20 | 6.45 | 13.06 | 15.26 |

EXAMPLE 4 a 1,3-(3-thiocyanatopropyl)-1,1,3,3-tetramethoxy disiloxane

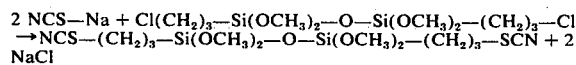

2 NCS—Na + Cl(CH$_2$)$_3$—Si(OCH$_3$)$_2$—O—Si(OCH$_3$)$_2$—(CH$_2$)$_3$—Cl
→NCS—(CH$_2$)$_3$—Si(OCH$_3$)$_2$—O—Si(OCH$_3$)$_2$—(CH$_2$)$_3$—SCN + 2 NaCl 45.2 grams of sodium thiocyanate were dissolved in 300 ml. of dimethylformamide and the solution heated to 140° C. Then there were added in about 60 minutes 98 grams of 1,3-(3-chloropropyl)-1,1,3,3-tetramethoxy disiloxane. After a further 30 minutes heating the reaction was practically completed. After cooling the separated sodium chloride was filtered off over a Seitz filter and the solvent removed by vacuum distillation. The liquid remaining behind was 1,3-(3-thiocyanatopropyl)-1,1,3,3-tetramethoxy disiloxane. Yield 95% based on the weight of the 1,3-(3-chloropropyl)-1,1,3,3-tetramethoxy disiloxane.

| Analysis | C | H | Si | N | S |
|---|---|---|---|---|---|
| Calculated (%) | 36.34 | 6.10 | 14.16 | 7.06 | 16.12 |
| Found (%) | 36.20 | 6.02 | 13.97 | 7.10 | 15.95 |

The 1,3-(3-thiocyanatopropyl)-1,1,3,3-tetramethoxy disiloxane was further defined by its IR-, NMR- and mass-spectra.

It is already known that 3-mercaptopropyl trimethoxy silane when used in natural rubber-silica mixtures reduces the strength of the crude mixture and raises the modulus values of the vulcanizates considerably as well as their rebound and shore hardness.

On the contrary the working properties of the mixtures are disadvantageously influenced, for example, the scorch time is greatly shortened. This means a reduction of the working safety. Further the Defo elasticity (see following Table I) is greatly increased which indicates an increase in the elastic rubber portion in the crude mixture and results in increased difficulties in their further working, for example, in extruding processes.

On the contrary it has now been found that the compounds of the invention on the one hand extensively produce the advantages of 3-mercaptopropyl trimethoxy silane but on the other hand more favorably influence the working properties of the rubber-filler mixtures. Furthermore, many of the compounds of the invention are accessible in a very economical manner because of their simple process of production with good yields and the ready availability of the starting materials and in addition are excellent for industrial duty.

A process is already known for the production of organosilicon sulfides wherein, among others, halogenethyl alkoxysilanes are reacted with alkali metal or alkaline earth metals salts of organic sulfides or sulfidic compounds (German Offenlegungsschrift No. 1,911,227). The compounds produced in this manner can be used as adhesive means or as intermediates for the production of water repellant agents or oxidation inhibitors.

The sulfur containing organo-organooxysilanes can be added directly, for example, to the rubber mixture. In this connection it is not necessary to hydrolyze the organo-organooxysilanes before the addition. Apparently, the moisture present in the mixture causes a partial hydrolysis which, for example, is necessary in the presence of silica containing compounds or silica fillers to produce siloxane bridges or in the presence of other inorganic materials in the starting mixture for building other bonds, for example, oxygen bridges through the splitting out of water from hydroxyl groups.

The sulfur containing organo-organooxysilanes can, however, with advantage must not be used coated on inorganic materials, for example, as fillers which means a process advantage.

Advantageously the inorganic filler material can be a mixture of at least two different rubber reinforcing fillers, e.g. silica and carbon black. The inorganic filler material may be introduced into the composition per se or pretreated with the said sulfur containing organo-organooxysilanes, e.g. coated with the sulfur containing organo-organooxysilanes or the filler material may be sprayed or dusted with said sulfur containing organo-organooxysilanes.

EXAMPLES V to VIII (Amounts in Parts by Weight)

TABLE I

| Test Mixture | 1 | 2 | 5 | 6 | 7 | 8 |
|---|---|---|---|---|---|---|
| styrene-butadiene rubber (Type 1500) | 100 | 100 | 100 | 100 | 100 | 100 |
| precipitated silica (ULTRASIL VN3) | 40 | 40 | 40 | 40 | 40 | 40 |
| zinc oxide | 4 | 4 | 4 | 4 | 4 | 4 |
| stearic acid | 2 | 2 | 2 | 2 | 2 | 2 |
| dibenzothiazyl-disulfide | 1.5 | 1.5 | 1.5 | 1.5 | 1.5 | 1.5 |
| diphenylguanidine | 1.5 | 1.5 | 1.5 | 1.5 | 1.5 | 1.5 |
| sulfur | 2.75 | 2.75 | 2.75 | 2.75 | 2.75 | 2.75 |

EXAMPLES V to VIII-continued (Amounts in Parts by Weight)

TABLE I

| Test Mixture | 1 | 2 | 5 | 6 | 7 | 8 |
|---|---|---|---|---|---|---|
| 3-mercaptopropyl trimethoxy silane (according to the state of the art) | — | 1.5 | — | — | — | — |
| Example V 3-thiocyanatopropyl triethoxy silane | — | — | 1.5 | — | — | — |
| Example VI 3-thiocyanatopropyl tri-n-butoxy silane | — | — | — | 1.5 | — | — |
| Example VII 3-triethoxysilyl-propyl-ethyl-xanthogenate | — | — | — | — | 1.5 | — |
| Example VIII 2-diethylamino-4-mercapto-6-(3-triethoxysilyl-propyl)-thiotriazine | — | — | — | — | — | 1.5 |

The vulcanization of the mixture took place at 160° C. and the vulcanization time was 40 minutes.

TABLE I

| Test Mixture | TEST RESULTS | | | | | |
|---|---|---|---|---|---|---|
| | 1 | 2 | 5 | 6 | 7 | 8 |
| Defo hardness[2] (g) | 3050 | 2200 | 1950 | 2250 | 1900 | 2300 |
| Defo elasticity[2] (%) | 16 | 33 | 21 | 22 | 29 | 23 |
| Mooney-Scorch time[3] (min.) | 25 | 5 | 17 | 20 | 11 | 13 |
| Mooney-Cure time[3] (min.) | 33 | 6 | 21 | 25 | 15 | 17 |
| Tensile strength[4] (kp/cm$^2$) | 154 | 152 | 156 | 149 | 158 | 151 |
| Modulus 300%[4] (kp/cm$^2$) | 55 | 134 | 120 | 117 | 130 | 118 |
| Elongation at break[4] (%) | 530 | 365 | 330 | 350 | 345 | 310 |
| Rebound[5] (%) | 43 | 47 | 47 | 46 | 47 | 44 |
| Shore hardness[6] | 71 | 74 | 74 | 74 | 73 | 73 |
| Permanent Extension[7] (%) | 14 | 8 | 7 | 7 | 7 | 7 |

[2]determined according to German Industry Standarts (DIN) 53514
[3]determined according to DIN 53524 (the Mooney scorch time is also designated as pre-vulcanization time $t_5$ and the Mooney cure time as pre-vulcanization time $t_{35}$)
[4]determined according to DIN 53504
[5]determined according to DIN 53512
[6] determined according to DIN 53505
[7]measured one hour after tearing the ring (ring tearing method; see DIN 53504)

The reduction of the Defo hardness of the test mixtures 5 to 8 (Table I) is about one third as compared to mixture 1 and points to their easier workability.

The increase in modulus to more than double that of the blank is related to a high degree of crosslinking.

The increase in rebound compared to the blank indicates more favorable dynamic properties. The increase of the shore hardness compared to the blank can otherwise frequently only be attained by increase in the portion of filler in the mixture.

Finally, the reduction of the permanent extension compared to the blank is interpreted as an important improvement of the performance properties.

Compared to test mixtures No. 2 (state of the art) there is shown a definitely more favorable relation with regard to the Defo elasticity and pre-vulcanization time $t_5$ as well as $t_{35}$ which makes it substantially easier or first makes it possible to handle such a mixture in the plant.

EXAMPLE IX

It is known that zinc oxide and stearic acid are not absolutely required to vulcanize rubber-silica mixtures. The action of 3-thiocyanatopropyl trimethoxy silane in a mixture free of zinc oxide and stearic acid is shown in the following.

TABLE II

| Test Mixture | 9 | 10 |
|---|---|---|
| styrene-butadiene rubber (Type 1500) | 100 | 100 |
| precipitated silica (ULTRASIL VN3) | 40 | 60 |
| dibenzothiazyldisulfide | 1.5 | 1.5 |
| diphenylguanidine | 1.5 | 1.5 |
| sulfur | 2.75 | 2.75 |
| 3-thiocyanatopropyl trimethoxy silane | — | 1.5 |

The vulcanization was carried out at 160° C. and the vulcanization time was 60 minutes.

TEST RESULTS

| Test Mixture | 9 | 10 |
|---|---|---|
| Defo hardness (g) | 2900 | 2000 |
| Defo elasticity (%) | 25 | 22 |
| Mooney-Scorch time (min.) | 11 | 11 |
| Mooney-Cure time (min.) | 15 | 15 |
| Tensile strength (kp/cm$^2$) | 153 | 168 |
| Modulus 300% (kp/cm$^2$) | 73 | 144 |
| Elongation at break (%) | 425 | 330 |
| Rebound (%) | 42 | 44 |
| Shore hardness | 72 | 75 |

TEST RESULTS-continued

| Test Mixture | 9 | 10 |
| --- | --- | --- |
| Permanent extension (%) | 12 | 7 |

The measurements were made as in examples V to VIII (Table I). The advantages of test mixture 10 are essentially equal to those in the previous examples.

EXAMPLE X

To determine wether the sulfur containing organo-organooxysilanes of the invention are also suited for use after they have previously been contacted with the filler 3-thiocyanatopropyl triethoxy silane as a test substance was dissolved in ethyl alcohol, then the ULTRASIL VN3 was introduced into the solution and finally the solvent was removed. The proportions were so chosen that exactly 40 parts of ULTRASIL VN3 and 1.5 parts of 3-thiocyanatopropyl triethoxy silane were present in both mixtures. The test took place with the same mixture 5 and in the same manner as is given in Table I.

In the test mixture 11, however, the ULTRASIL VN3 and the 3-thiocyanatopropyl triethoxy silane were mixed in separately, in the test mixture 12 on the contrary there was used ULTRASIL VN3 loaded with the 3-thiocyanatopropyl triethoxy silane (produced as set forth above).

TABLE III

| Test Mixture | (Test Results) 11 | 12 |
| --- | --- | --- |
| Defo hardness (g) | 2150 | 2200 |
| Defo elasticity (%) | 23 | 20 |
| Mooney-Scorch time (min.) | 17 | 17 |
| Mooney-Cure time (min.) | 20 | 21 |
| Tensile strength (kp/cm$^2$) | 144 | 152 |
| Modulus 300% (kp/cm$^2$) | 116 | 115 |
| Elongation at break (%) | 340 | 365 |
| Rebound (%) | 45 | 44 |
| Shore hardness | 72 | 73 |
| Permanent extension (%) | 7 | 9 |

From these values it is evident that there can be employed with success the previous coating of a silica filler with 3-thiocyanatopropyl triethoxy silane.

This method of operation has important industrial uses as a consequence. The sulfur containing organo-organooxysilanes can be precipitated from aqueous or nonaqueous solution on the particles of the inorganic material, for example, material consisting of silica or SiO$_2$ or material containing these or silicious materials or silicates of natural or synthetic origin or also silicate glass products. The materials so prepared are used, for example, as fillers strengthening agents or additive materials in polymers, preferably in elastomers or in mixtures containing these before carrying out the crosslinking. Especially well suited for this purpose are the water soluble 3-thiocyanatopropyl trimethoxy silane and 3-thiocyanatopropyl triethoxy silane.

EXAMPLE XI

The activity of 3-thiocyanatopropyl tri-n-propoxy silane is shown in the following natural rubber mixture containing AEROSIL, i.e. pyrogenic silica. The amounts are given in parts by weight. The measurements were made in the same manner as in Table I.

TABLE IV

| Test Mixture | 13 | 14 |
| --- | --- | --- |
| ribbed smoked sheets I | 100 | 100 |
| AEROSIL (130 m$^2$/g BET surface) | 40 | 40 |
| zinc oxide | 4 | 4 |
| stearic acid | 2 | 2 |
| dibenzothiazyldisulfide | 1.5 | 1.5 |
| diphenylguanidine | 1.5 | 1.5 |
| sulfur | 2.75 | 2.75 |
| 3-thiocyanatopropyl tri-n-propoxy silane | — | 1.5 |

The vulcanization time was accomplished at 145° C. and the vulcanization time was 20 minutes.

| TEST RESULTS | | |
| --- | --- | --- |
| Test Mixture | 13 | 14 |
| Defo hardness (g) | 2300 | 1650 |
| Defo elasticity (%) | 29 | 24 |
| Mooney-Scorch time (min.) | 18 | 13 |
| Mooney-Cure time (min.) | 21 | 15 |
| Tensile strength (kp/cm$^2$) | 264 | 284 |
| Modulus 300% (kp/cm$^2$) | 670 | 600 |
| Rebound (%) | 52 | 56 |
| Shore hardness | 64 | 66 |

There was obtained with natural rubber and a pyrogenic silica in principle the same advantageous activity as with precipitated silica in styrene-butadiene rubber.

The following example shows that a normal vulcanization process and customary industrial rubber data can be produced with the compounds of the present invention without addition of conventional accelerators and/or activators.

EXAMPLE XII

The starting mixture (Test Mixture 15) was composed of the following constitutents (in parts by weight).

| | |
| --- | --- |
| styrene-butadiene rubber (Type 1500) | 100 |
| ULTRASIL VN3 | 40 |
| zinc oxide | 4 |
| stearic acid | 2 |
| 3-thiocyanatopropyl triethoxy silane | 3 |
| sulfur | 2.75 |

The vulcanization was carried out at 160° C. the vulcanization time was 60 minutes and the following test results were obtained.

| | |
| --- | --- |
| Tensile strength (kp/cm$^2$) | 206 |
| Modulus 300% (kp/cm$^2$) | 56 |
| Modulus 500% (kp/cm$^2$) | 124 |
| Elongation at break (%) | 670 |
| Rebound (%) | 40 |
| Shore hardness | 66 |

The new sulfur containing organo-organooxysilanes, as stated, in the widest sense are outstandingly useful in crosslinkable or vulcanizable mixtures of organic polymers, inorganic materials and suitable crosslinking or vulcanizing agents or systems. As organic polymers there are especially employed the known elastomers, and of these first of all natural and synthetic rubbers. To these crosslinkable mixture of organic polymers, inorganic materials and crosslinking agents there can be added in a given case known reaction accelerators and furthermore in a given case one or more compounds of the group of antioxidants (antiagers), processing aids, plasticizers and heat or light stabilizers which are known in plastic technology. For vulcanization there are added to the mixture vulcanization agents, especially sulfur and/or sulfur liberating compounds, e.g. N,N'-dithiobis morpholine, dipentamethylene thiuramtetrasulfide, N,N'-dithiobis hexahydro-2H-azepinone-(2), 2-benzthiazyl dithio-N-morpholide etc. and in a given case vulcanization accelerators; additionally there can be included and homogeneously distributed in these mixtures one or more compounds of the group of rubber antioxidants, processing aids, pigments and stearic acid as well as zinc oxide which all are known and used in the rubber art. The sulfur containing organo-organooxysilane manifestly acts in the crosslinking or vulcanization reaction.

It is evident to those skilled in the art that compounds of the class A (b) which contain the thioether group must contain one or more additional vulcanization active groups as for example the 2,4-dimercapto-1,3,5-triazinyl group and/or one or more additional vulcanizable groups as for instance the allyl group or other groups having nonbenzoid carbon to carbon unsaturation.

The named inorganic materials can be added as fillers, pigments, fibers or the like. Of especial advantage in this regard there are preferably added as inorganic filler materials substances which are designated in the rubber industry as reinforcing fillers. These preferred additives are especially based on silica of various origin or such silica (silicon dioxide) containing oxide mixtures and mixed oxides, namely oxide compounds of metals such as aluminium, magnesium, calcium, barium, zinc, iron, zirconium or titanium, e.g. alumina, magnesium oxide, calcium oxide, barium oxide, zinc oxide, ferric oxide, zirconia, titania, aluminium silicate, talc, asbestos etc. including oxides (mixed oxides) of two or more of said metals.

Those oxide compounds which are also designated as highly dispersed or finely divided materials are preferably produced in the gas phase by oxydative or hydrolytic decompostion, namely emanating from volatile metal or metalloid halogenides. Also well suited are those obtained by precipitation of a soluble compound of the above named elements, e.g. of a soluble silicate. In a given case there also can be employed as the inorganic materials natural silicates or silicates produced chemically such as asbestos, wollastonite, kaoline, talc as well as quartz, sand, clay, carbon black or the like or glass in the form of fibers, mats, fabrics or other fiber products or structures as well as compact varieties or metal fibers, e.g. aluminium or steel fibers.

The new sulfur containing organo-organooxysilanes have valuable properties; they possess in the sense of the present invention bifunctional activity. The new oxysilanes promote, for example, the vulcanization or crosslinking of elastomer or rubber mixtures. Even without addition of conventional accelerators or activators there are obtained with the compounds of the invention at the customary crosslinking or vulcanization temperatures and times vulcanizates with normal use and test data. They also act as coupling agents. The binding (coupling) capacity, for example, to silica or silicate surfaces occurs through the trialkoxysilane group by chemical reaction forming Si- O- Si bridges or by chemisorption. This binding property is also true of the compounds of group A (*b*) of the invention.

The activity of the sulfur containing organo-organooxysilanes is especially advantageous in rubber mixtures for the production of tires which contain the so-called light reinforcing fillers, also they develop valuable properties in tire production using glass fibers, yarn, cloth, fiber quilt or similar structures, wherein there are employed, for example, styrene-butadiene rubber, butadiene rubber, natural rubber, cis-isoprene rubber or the like elastomers. Thus it is possible for example to produce white or colored tires or tire treads with the help of the new compounds from rubber and light reinforcing fillers. Among the usable types of rubbers there should also be included the usual known diene rubbers, nitrile rubbers, terpolymers, for example, of ethylene, propylene and dienes or trienes etc.

The sulfur containing organo-organooxysilanes can be added in an amount of 0.1 to 20%, preferably 0.5 to 10% based on the weight of the organic polymer.

For the vulcanization of the rubbery polymers there can be added sulfur and/or sulfur liberating compounds in an amount of 0.2 to 4 weight parts per 100 weight parts of the rubbery polymer of the types mentioned above.

The inorganic filler material can be added to the mixtures (compositions) in an amount of 5 to 100 parts by weight (preferably 10 to 90 parts by weight) per 100 parts by weight of said rubbery polymers. These compositions may include 2 to 5 parts by weight of zinc oxide and 0.5 to 3 parts by weight of an accelerator.

EXAMPLE XIII

The procedure of Example 4 was repeated replacing the 3-chloropropyl triethoxy silane by an equimolar amount of 3-chloropropyl trimethoxy silane to produce 2-diethylamino-4-mercapto-6-(3-trimethoxysilylpropyl)-thiotriazine. The structure was confirmed by elemental analysis.

The 2-diethylamino-4-mercapto-6-(3-trimethoxysilylpropyl)-thiotriazine was employed in an amount of 1.5 parts in the same basic styrene-butadiene rubber formulation as Example VIII in Table I in place of the 2-diethylamino-4-mercapto-6-(3-triethoxysilylpropyl)-thiotriazine. The rubber mixture was produced on the roller mill and vulcanization was carried out under the same conditions as with the Table I formulations, namely 160°C. for 40 minutes. The results were as follows:

| | |
|---|---|
| Defo hardness (g) | 2400 |
| Defo elasticity (%) | 30 |
| Mooney-Scorch time (min.) | 13 |
| Mooney-Cure time (min.) | 17 |
| Tensile strength (kp./cm$^2$) | 127 |
| Modulus 300% (kp./cm$^2$) | 123 |
| Shore hardness | 73 |
| Permanent Extension (%) | 5 |

The commercial material, gamma mercaptopropyltrimethoxysilane (available commercially as A-189 from Union Carbide Corp.) has the values set forth in Table I Test Mixture 2.

The following observations may be noted. The Permanent Extension (Permanent Elongation) for the product of Example XIII is practically the same as for the mercaptopropyltrimethoxy silane. The Permanent Extension is an indication for the degree of cross-linking. In comparison to the product of Example XIII, the Mooney-Scorch and Mooney-Cure times of 5 and 6 minutes using A-189 are so short that this silane cannot be used in practice within a very limited area. Also in practice the mixture containing A-189 tends to be vulcanized on the rolls. In contrast the mixture containing the silane of the invention has sufficient working safety. The Mooney-Scorch and Mooney-cure times are more than double as long as those for A-189. This is a substantial advantage over A-189.

It has been found that a preferred group of compounds within the invention have the formula R-S-X-Z where R is

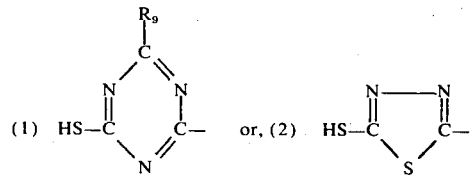

where $R_9$ is hydrogen

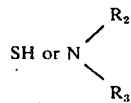

and $R_2$ and $R_3$ are hydrogen or a lower alkyl, preferably hydrogen or alkyl of 1 to 5 carbon atoms, X is either (1) a divalent acyclic or cyclic hydrocarbon group having at least 3 carbon atoms in the main chain and when cyclic not over 18 carbon atoms or (2) such a cyclic hydrocarbon group having a hydrogen replaced by fluorine, pseudohalogen, phenyl, halophenyl, monoalkyl or dialkyl phenyl in which the alkyl group contains 1 to 3 carbon atoms and Z is Si R'' (OR')$_2$-Si(OR')$_3$; -Si(OR')$_2$-O-Si(OR')$_3$; or -Si(OR')$_2$-O-Si(OR')$_2$-X-R where R' and R'' are alkyl of 1 to 12 carbon atoms.

More preferably X is a straight or branched chain hydrocarbon group having 3 to 18 carbon atoms (CnH$_{2n}$ where n is 3 to 18). Still more preferably X is (CH$_2$)$_n$ and most preferably $n$ is 3, i.e., X is trimethylene or propylene.

Z is preferably -SiR'' (OR')$_2$ or -Si(OR')$_3$ wherein R'' and R' are alkyl of 1 to 4 carbon atoms.

In addition to the compounds set forth above within the invention there can be mentioned 2-mercapto-5-(3-trimethoxysilyl propyl)-thio-1,3,4-thiodiazole; 2-mercapto-5-(18-trimethoxysilyl propyl)-thiodiazole; 2-diamylamino-4-mercapto-6-(3-triisopropoxysilyl propyl)-thiotriazine; 2-diethylamino-4-mercapto-6-(3-diethoxy methylsilyl propyl)-thiotriazine.

What is claimed is:

1. A compound having the formula R-S-X-Z where R is the heterocyclic group

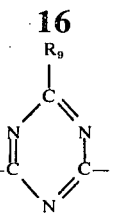

where $R_9$ is hydrogen,

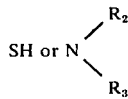

and $R_2$ and $R_3$ are hydrogen or a lower alkyl, X is an alkylene group having at least 3 carbon atoms in the main chain and not over 18 carbon atoms and Z is SiR''(OR')$_2$; Si(OR')$_3$; -Si(OR')$_2$-O-Si(OR')$_3$; or Si(OR')$_2$-O-Si(OR')$_2$-X-R where R' and R'' are alkyl of 1 to 12 carbon atoms.

2. A compound according to claim 1 wherein X is alkylene of 3 to 18 carbon atoms and Z is Si R'' (OR')$_2$; or Si(OR')$_3$.

3. A compound according to claim 1 wherein $R_2$ and $R_3$ both are alkyl of 1 to 5 carbon atoms.

4. A compound according to claim 2 wherein $R_2$ and $R_3$ are both hydrogen.

5. A compound according to claim 1 wherein $R_2$ is hydrogen and $R_3$ is alkyl of 1 to 5 carbon atoms.

6. A compound according to claim 1 wherein X is alkylene of 3 to 5 carbon atoms, Z is Si(OR')$_3$ and R' is alkyl of 1 to 4 carbon atoms.

7. A compound according to claim 6 wherein X is alkylene of 3 carbon atoms.

8. A compound according to claim 1 which is 2-diethylamino-4-mercapto-6-(3-triethoxysilylpropyl)-thiotriazine.

9. A compound according to claim 1 which is 2-diethylamino-4-mercapto-6-(3-trimethoxysilylpropyl)-thiotrizine.

10. A compound according to claim 1 wherein $R_9$ is

11. A compound according to claim 10 wherein Z is SiR''(OR')$_2$ or Si(OR')$_3$.

12. A compound according to claim 11 wherein $R_2$ and $R_3$ are both alkyl of 1 to 5 carbon atoms.

13. A compound according to claim 12 wherein X is alkylene of 3 to 5 carbon atoms, Z is Si(OR')$_3$ and R' is alkyl of 1 to 4 carbon atoms.

14. A compound according to claim 13 wherein X is alkylene of 3 carbon atoms.

* * * * *